United States Patent [19]
Cabrera et al.

[11] Patent Number: 5,104,547
[45] Date of Patent: Apr. 14, 1992

[54] SEPARATING MATERIALS FOR CHROMATOGRAPHY COMPRISING CYCLODEXTRIN CHEMICALLY BONDED TO A SUPPORT VIA A CARBAMIC ACID GROUP

[75] Inventors: Karin Cabrera, Gross-Gerau; Gisela Schwinn, Darmstadt; Dieter Lubda, Bensheim-Auerbach, all of Fed. Rep. of Germany

[73] Assignee: Merck Patent Gesellschaft MIT Beschräkter Haftung, Darmstadt, Fed. Rep. of Germany

[21] Appl. No.: 665,113

[22] Filed: Mar. 6, 1991

[30] Foreign Application Priority Data

Mar. 6, 1990 [DE] Fed. Rep. of Germany ....... 4006923

[51] Int. Cl.$^5$ .............................................. B01D 15/08
[52] U.S. Cl. ................... 210/656; 210/198.2; 210/502.1; 528/38; 536/103
[58] Field of Search .................... 536/103; 210/198.2, 210/656, 502.1, 635; 528/38

[56] References Cited

U.S. PATENT DOCUMENTS

| | | | |
|---|---|---|---|
| 3,673,233 | 6/1972 | Golitz et al. | 528/38 |
| 4,322,310 | 3/1982 | House | 210/635 |
| 4,324,681 | 4/1982 | House | 210/635 |
| 4,517,241 | 3/1985 | Alpert | 210/659 |
| 4,539,399 | 9/1985 | Armstrong | 210/502.1 |
| 4,781,858 | 11/1988 | Mizukami et al. | 210/635 |
| 4,781,977 | 11/1988 | Yagi et al. | 536/103 |
| 4,867,884 | 9/1989 | Rendlemann, Jr. | 210/656 |
| 5,017,290 | 5/1991 | Nami Koshi et al. | 210/656 |

*Primary Examiner*—Robert A. Dawson
*Assistant Examiner*—Sun Uk Kim
*Attorney, Agent, or Firm*—Millen, White & Zelano

[57] ABSTRACT

The invention relates to a separating material for chromatography in which cyclodextrin is bonded to a support via a carbamic acid group.

5 Claims, 2 Drawing Sheets

SEPARATING MATERIALS FOR CHROMATOGRAPHY COMPRISING CYCLODEXTRIN CHEMICALLY BONDED TO A SUPPORT VIA A CARBAMIC ACID GROUP

BACKGROUND OF THE INVENTION

The invention relates to a novel separating material for chromatography which essentially comprises a support and cyclodextrin chemically bonded thereto via a carbamic acid group, to the production thereof, and to the use thereof for improved separation of mixtures of substances and enantiomers by chromatography.

The use of cyclodextrins in the chromatographic separation and purification processes is described, for example, in a review by W.L. Hinze, Separation and Purification Methods, 10 (2) 159-237 (1981). However, when cyclodextrin solutions are used as the mobile phase, considerable problems are caused by the inadequate solubility of the 8-cyclodextrins. Cyclodextrin has been experimentally tested as the stationary phase. To this end, polymeric materials were prepared. However, these polymeric gels require a long analysis time and also exhibit low mechanical stability, meaning that these materials are not suitable for high-performance liquid chromatography (HPLC).

Attempts have therefore been made to bond cyclodextrins to a solid matrix. Cyclodextrins are known which are bonded to silica gel via amine or amide bonds. However, these bonds were hydrolytically unstable. It was therefore not possible to work in the aqueous phase. U.S. Pat. No. 4,539,399 describes cyclodextrins coupled to silica gel via a bond without nitrogen. The bond between cyclodextrin and the support generally takes place here via an ether bridge. However, the disadvantage of these materials is that a large number of enantiomeric mixtures, for example pharmaceutical active ingredients or sugar-like derivatives, cannot be separated using these materials.

SUMMARY OF THE INVENTION

The object of the present invention was therefore to find a novel, improved material comprising a support and cyclodextrin bonded chemically thereto, which is universally applicable in the chromatographic separation (HPLC, LC, TLC) of enantiomeric mixtures and achieves improved separation properties.

Upon further study of the specification and appended claims, further objects and advantages of this invention will become apparent to those skilled in the art.

Surprisingly, it has now been found that a separating material in which the cyclodextrin is bonded to the support via a carbamic acid group satisfies the above-mentioned criteria in an excellent manner.

The invention therefore relates to a separating material for chromatography, essentially comprising a support and cyclodextrin chemically bonded to this support, characterized in that the cyclodextrin is bonded via a carbamic acid group.

The invention furthermore relates to a process for the production of this separating material in which the cyclodextrin is first activated by reaction with a chloroformic acid ester, and this activated cyclodextrin is then either a) reacted with an aminosilane containing at least one further reactive group, to give the corresponding cyclodextrin-silane derivative, and this reactive derivative is then allowed to react with the support in a silanization reaction, or b) coupled directly with a support which has been modified by a silanization reaction with amino groups, a carbamic acid group in each case being formed between the cyclodextrin and the radical.

The invention furthermore relates to the use of these separating materials for the chromatographic separation of substance mixtures and in particular of enantiomers.

Supports which can be employed are silica gel or alternatively other inorganic materials, such as, for example, $Al_2O_3$, $TiO_2$ or $ZrO_2$, or alternatively synthetic polymer supports, preferably already carrying free $NH_2$ groups.

Examples of suitable synthetic polymer supports are polymers made from (meth)acrylamide derivatives or vinyl derivatives.

The support employed is preferably silica gel, which is commercially available in a wide range of different shapes and sizes.

The material according to the invention can thus be produced by two different methods. However, the first and important step in both variants is the same. The cyclodextrin, which may be in α-, β-, γ- or gamma-form, β-cyclodextrin being particularly preferred, is converted into an activated cyclodextrin by reaction with a chloroformic acid ester. In principle, any chloroformic acid ester can be employed for this purpose. Preference is given to esters of this type in which the ester group is a good leaving group. Very particularly preferred activating agents have proven to be p-nitrophenyl chloroformate and N-succinimido chloroformate. This reaction is preferably carried out at room temperature in the presence of a base.

The cyclodextrin activated in this way is, in variant a), now reacted further as follows: the cyclodextrin is reacted with an aminosilane having at least one further reactive group in order to subsequently be able to react with the support, the carbamoyl bond already being formed between the cyclodextrin and the silane derivative. The aminosilane employed here may be any customary silane known to those skilled in the art which fulfills two criteria: they must contain an amino group and at least one further reactive group which is suitable for a silanization reaction with the support, such as, for example, an alkoxy group or a halogen.

Particularly suitable silanes are those which conform to the general formula below:

where
R is alkyl, aryl or aralkyl having up to 20 carbon atoms, in each case containing at least one amino group, wherein one or more non-adjacent $CH_2$ groups can be substituted by NH- groups, and
X is alkoxy, aralkoxy or alkyl having up to 20 carbon atoms, with the proviso that at least one X is alkoxy or aralkoxy.

Such silanizing agents are known in large number from the literature or can be prepared analogously to known methods. (See "Porous Silica", Unger, K.K., Elsevier Scientific Pub. Co., Amsterdam-Oxford-New York, 1979.) They are suitable for the processing according to the invention in the same way as for known modifications of surfaces of sorbents.

Very particular preference is given to silanes such as, for example, 3-aminopropyltrimethoxysilane, 3-aminopropyltriethoxysilane, 3-(2-aminoethyl)aminopropyltriethoxysilane and 3-(2-aminoethyl)aminopropyltrimethoxysilane.

The reaction is expediently carried out at room temperature with a reaction duration of—depending on the batch size—from 30 minutes to a few hours. The cyclodextrin is thereby bonded to the silane via a carbamic acid group.

In the third step, this cyclodextrin-silane derivative is coupled via a reactive group in a generally known silanization reaction to the support carrying hydroxyl groups to give the end product.

The conditions of this reaction may be freely chosen from the literature by a person skilled in the art; the reaction is preferably carried out at room temperature and takes a few hours.

The support is expediently dried before the reaction.

In the second variant, the cyclodextrin is first again activated as described. This activated cyclodextrin is subsequently coupled with a support which has already been modified with amino groups. This $NH_2$-modified material can either be obtained commercially in finished form or prepared by a silanization reaction of the support with an appropriate aminosilane. The aminosilanes described above are suitable for this purpose.

Here too, a carbamic acid group is formed between the cyclodextrin and the $NH_2$-groups of the support. The reaction is again preferably carried out at room temperature.

The connection between the support and the cyclodextrin may comprise a relatively short or relatively long chain. This depends entirely on the silane employed. The chain preferably has 3-20 atoms and may contain nitrogen or oxygen atoms in addition to carbon atoms.

It is, of course, also possible to prepare materials according to the invention which simultaneously contain two different cyclodextrins in bonded form, such as, for example, β- and gamma-cyclodextrin, by the methods described here. Such materials likewise exhibit very broad selectivity.

The amount of cyclodextrin reacted with the support preferably ranges from 1 to 80 g, most preferably 15 to 50 g, per 100 gms of silica gel support.

The material according to the invention can, if desired, furthermore be subjected to a so-called "end-capping" reaction. In this, the remaining hydroxyl groups on the silica gel surface are reacted in a known manner with a reactive silane, such as, for example, trimethylchlorosilane, or alternatively hexamethyldisilazane, in order to complete the blocking of the surface hydroxyl groups.

The novel materials according to the invention are excellent separating materials for the chromatographic separation of a wide range of substances, in particular of enantiomeric mixtures. They are universally applicable, for example also for pharmaceutical active ingredients or for sugar-like derivatives, which could hitherto not be separated using the materials known from the prior art.

The materials according to the invention are preferably employed in LC or HPLC. However, they can also be applied to plates in a known manner and thus employed in thin-layer chromatography.

Figure 1:
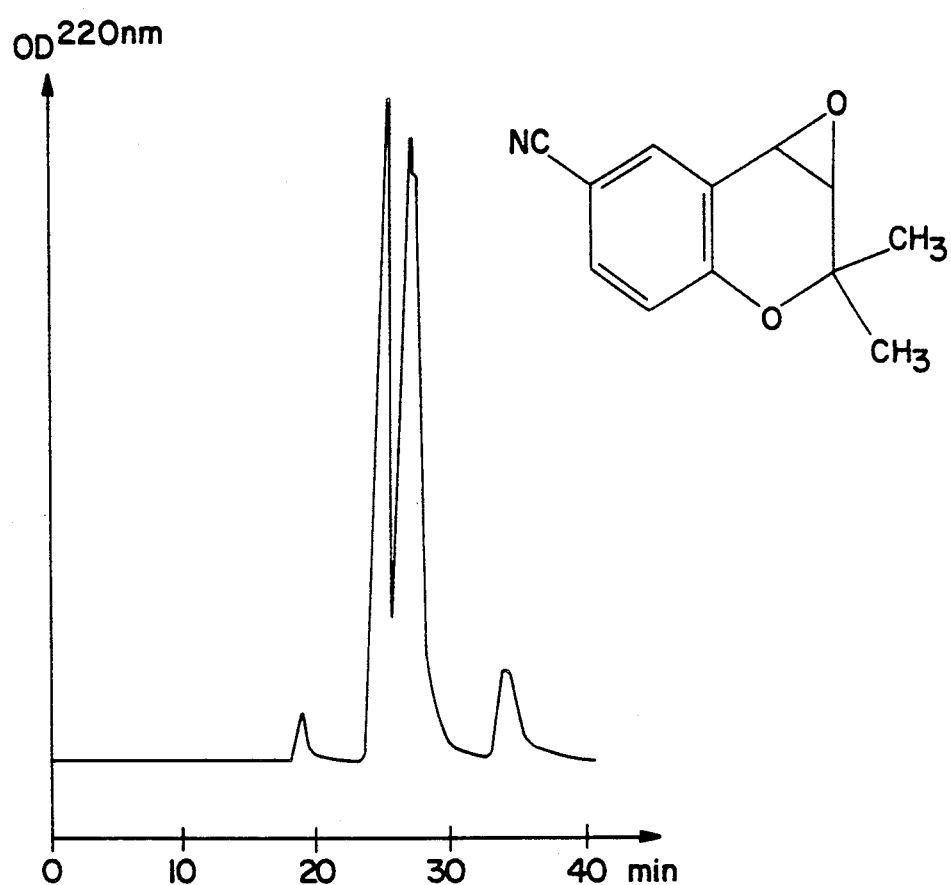
FIGS. 1 and 2 show elution diagrams and the formulas of the racemates separated. Details are given in Example 4.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, cited above and below, and of corresponding application Federal Republic of Germany P 40 06 923.0, filed Mar. 6, 1990, are hereby incorporated by reference.

E X A M p L E S

Production of the materials according to the invention.

1. β-Cyclodextrin is dried for 4 hours at 100° in vacuo.

4.4 mmol of β-cyclodextrin are dissolved in 50 ml of pyridine and reacted with 30.8 mmol of p-nitrophenyl chloroformate for 2 hours at 20° to give the activated β-cyclodextrin.

0.0 g of LiChrospher ® 100 $NH_2$ (E. Merck), a silica gel modified with 3-aminopropyl (3.85 μmol/m$^2$) with an average pore diameter of 100 Å and average particle size of 5 μm, which had previously been dried for 4 hours at 100° in vacuo were then added. The mixture was allowed to react for 4 hours at 20°, filtered through a glass frit and rinsed with pyridine, water, ethanol and petroleum ether (in this sequence).

A product is obtained which has the following CHN analysis: C: 9.6%, N: 0.8%; H: 1.62%.

2. 4.4 mmol of β-cyclodextrin (previously dried for 4 hours at 100° in vacuo) are treated in 50 ml of pyridine with 8.8 mmol of p-nitrophenyl chloroformate and activated for 2 hours at 20°. 1.17 g of 3-(2-aminoethyl)aminopropyltrimethoxysilane are subsequently added, and the mixture is stirred for 2 hours at 20°. 10.0 g LiChrospher ® 100 (E. Merck), a porous underivatized silica gel with an average pore diameter of 100 Å, a specific surface (BET) of 420 m$^2$/g and an average particle size of 10 μm, is added, and the mixture is stirred for 18 hours at 20° Work-up is analogous to Example 1.

A product is obtained which has the following CHN values: C: 5.0%; N: 0.7%; H 0.96%:

SEPARATION EXAMPLES

3. The material produced as in Example 1 is introduced into a column (LiChroCART ® 250-4), and the following myo-inosites are separated therewith under HPLC conditions:

| Substance | Eluent acetonitrile/ water | Flow rate ml/min | Detection UV | RT in minutes |
|---|---|---|---|---|
| DL-1-O-Benzyl myo-inosite | 1/99 | 1.0 | 220 nm | 11.21/12.57 |

| Substance | Eluent acetonitrile/ water | Flow rate ml/min | Detection UV | RT in minutes |
|---|---|---|---|---|
| DL-1-O-Benzyl 2,3-O-cyclo-hexylidene 6-O-butyryl myo-inosite | 10/90 | 1.0 | 220 nm | 13.78/15.57 |
| DL-1,4,5,6-Tetra-O-benzyl myo-inosite | 15/85 | 1.0 | 220 nm | 36.85/48.86 |

Separation of these substances into their D- and L-forms was excellent. By comparison, separation of these substances under the same conditions in a column filled with a material from the prior art (Cyclobond I, Astec) was investigated, but was negative. No separation could be achieved using this material.

4. The following potassium channel activators were separated into their optical antipodes analogously to Example 3 using the material according to the invention:

Eluent: MeOH/0.025M buffer, pH=2.5 20/80
Flow rate: 0.4 ml/min
Detection: UV 220 nm

| Substance | RT in min. |
|---|---|
| (±)-6-Cyano-3,4-epoxy-2,2-dimethylchroman | 24.50/26.36[1] |
| (±)-6-Cyano-3,4-epoxy-2,2,3-trimethylchroman | 45.38/56.22[2] |
| (±)-6-Cyano-2,2,3-trimethyl-4-(1,6-dihydro-6-oxopyridazin-3-yloxy)chroman-3-ol | 80.73/84.38[3] |
| (±)-6-Cyano-2,2-dimethyl-4-(1,6-dihydro-1-methyl-6-oxopyridazin-3-yloxy)chroman-3-ol | 42.19/54.52[2] |
| (±)-6-Cyano-2,2-dimethyl-4-(1,2-dihydro-2-oxopyridyl)chroman-3-ol | 18.48/20.82[2] |

Figure 2:
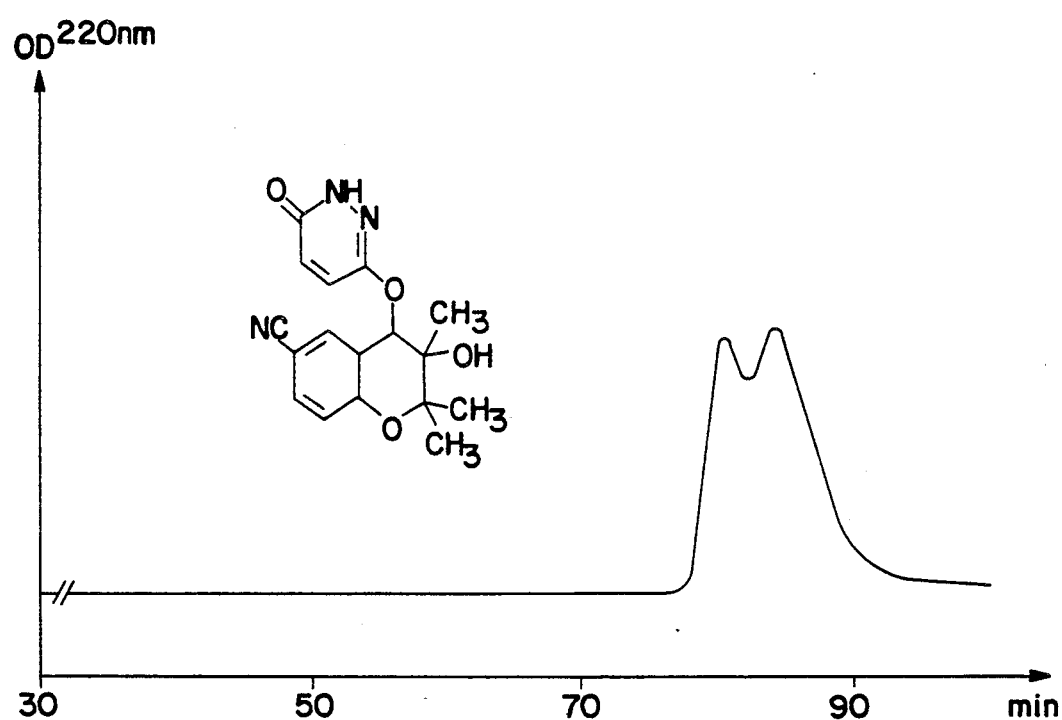

Remarks:
[1] See elution diagram (FIG. 1).
[2] (+) isomer eluted before (−) isomer.
[3] See elution diagram (FIG. 2).

These examples again show clearly that the novel material is highly suitable for separating pharmaceutical active ingredients.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A separating material for chromatography, which comprises a support having cyclodextrin chemically bonded thereto via a carbamic acid group.

2. A separating material as in claim 1, wherein the carbamic acid group is bound to an aminosilane group which is bound to the support.

3. A separating material as in claim 2, wherein the support is silica gel, $Al_2O_3$, $TiO_2$, $ZrO_2$ or a synthetic polymer carrying free $NH_2$ groups and the amino silane is of the formula $RSiX_3$ wherein R is alkyl, aryl or aralkyl having up to 20 carbon atoms, in each case containing at least one amino group, wherein one or more non-adjacent $CH_2$ groups can be substituted by NH-groups, and X is alkoxy, aralkoxy or alkyl having up to 20 carbon atoms, with the proviso that at least one X is alkoxy or aralkoxy.

4. A chromatographic separation process for the separation of substance mixtures, the improvement comprising utilizing a separating material for chromatography which comprises a support having cyclodextrin chemically bonded thereto via a carbamic acid group.

5. A chromatographic separation process for the separation of enantiomers, the improvement comprising utilizing silica gel having cyclodextrin chemically bonded thereto via a carbamic acid group.

* * * * *